United States Patent [19]

Ho Dac et al.

[11] Patent Number: 5,141,757
[45] Date of Patent: Aug. 25, 1992

[54] FLAVOURING AGENT

[75] Inventors: Thang Ho Dac; Robert D. Wood, both of Le Mont s/Lausanne; Alfred Woupeyi, Yverdon, all of Switzerland

[73] Assignee: Nestec S.A., Vevey, Switzerland

[21] Appl. No.: 565,517

[22] Filed: Aug. 10, 1990

[30] Foreign Application Priority Data

Nov. 27, 1989 [CH] Switzerland .................. 04234/89

[51] Int. Cl.$^5$ .................................................. A23J 3/34
[52] U.S. Cl. ........................................ 426/46; 426/44; 426/32; 426/42; 426/52
[58] Field of Search ................. 426/46, 44, 32, 42, 426/52

[56] References Cited

U.S. PATENT DOCUMENTS

| | | | |
|---|---|---|---|
| 3,857,966 | 12/1974 | Feldman | 426/46 |
| 3,857,967 | 12/1974 | Kikuchi et al. | 426/46 X |
| 3,912,822 | 10/1975 | Yokotsuka et al. | 426/44 |
| 3,914,436 | 10/1975 | Nakadai | 426/46 |

Primary Examiner—Joseph Golian
Attorney, Agent, or Firm—Vogt & O'Donnell

[57] ABSTRACT

A process for the production of a flavoring agent, in which an aqueous suspension of a protein-rich material is prepared, the proteins are solubilized by hydrolysis with a neutral or alkaline protease, the suspension is heat-treated at a mildly acidic pH value and is then ripened with koji enzymes.

14 Claims, No Drawings

FLAVOURING AGENT

BACKGROUND OF THE INVENTION

This invention relates to a process for the production of a flavouring agent by enzymatic hydrolysis of proteins.

Materials rich in proteins, such as for example oilseed cakes, pulses, cereal gluten or lactic proteins, are widely used in hydrolyzed form as a starting material in the composition of dehydrated or liquid soups, sauces and seasonings.

In this context, a peanut or soybean cake, for example, is normally subjected to hydrolysis with concentrated hydrochloric acid, the hydrolyzate is neutralized with sodium hydroxide, the insoluble fractions are removed, the hydrolyzate is optionally subjected to filtration, decoloration, concentration and/or drying and is then used as a flavouring agent as such, or after reaction with reducing sugars, for example.

A process such as this for the production of a flavouring agent by acidic hydrolysis of proteins is attended inter alia by the disadvantage that the amino acids produced during hydrolysis are degraded.

If, for this reason, it is preferred to subject a material rich in proteins to enzymatic hydrolysis, the familiar problem of bitterness of the hydrolyzate caused by bitter peptides produced during hydrolysis is encountered.

Various processes have been proposed with a view to avoiding or eliminating this bitterness, in particular by carrying out the enzymatic hydrolysis under such conditions that the production of bitter peptides is reduced, by extracting the bitter peptides from the hydrolyzate or by degrading the bitter peptides.

EP 223 560, for example, describes a process in which casein or an isolate of soya proteins is hydrolyzed with a proteinase, after which the bitterness of the product obtained is eliminated by rehydrolysis with an aminopeptidase derived from a strain of *Streptococcus lactis*.

SUMMARY OF THE INVENTION

The object of the present invention is to provide a process for the production of a flavouring agent by enzymatic hydrolysis of a material rich in common proteins without having to use purified exopeptidases to eliminate bitterness while at the same time providing the product with remarkable organoleptic qualities.

To this end, the process according to the invention for the production of a flavouring agent is characterized in that an aqueous suspension of a protein-rich material is prepared;

the proteins are solubilized by hydrolysis of the suspension with a protease at pH 6.0 to 11.0;

the suspension is heat-treated at pH 4.6 to 6.5: and the suspension is ripened with enzymes of koji.

The process according to the invention effectively permits the preparation, from common protein-rich materials such as a defatted soya flour or casein, of a flavouring agent having remarkable organoleptic qualities, namely, in an embodiment involving a relatively short ripening period, a pleasant and relatively neutral taste devoid of bitterness, and in an embodiment involving a longer ripening period, a stronger flavour but still without bitterness.

In the context of the invention, the term "koji" designates the product of fermentation, with a Koji culture, of a mixture of a protein source and a carbohydrate source, more particularly a mixture of a cooked pulse or oilseed and a cooked or roasted cereal, for example a mixture of cooked soya or haricot bean and cooked or roasted wheat or rice.

In the context of the invention, a koji culture is understood to be the culture of koji spores of the type available on the market, particularly in Japan or China, which in particular comprises spores of *Aspergillus oryzae* or *Aspergillus soyae*.

Similarly, in the context of the invention, the expression "halophilic yeast culture" is used in the sense of a culture of yeasts producing aromatic substances and alcohol, such as *Saccharomyces rouxii* for example, used for the traditional fermentation of a moromi obtained by mixing a koji and a brine in the traditional preparation of soya sauce.

Finally, the enzymatic activity of the protease is characterized in the present specification by the Anson unit (AU), as defined by Anson's analysis method (J. General Physiology 22, 1939, 79-89) modified by Novo Industri A/S.

DETAILED DESCRIPTION OF THE INVENTION

To carry out the process according to the invention, the protein-rich material may be selected from the group consisting of subdivided and defatted oilseeds or pulses, particularly defatted flours or cakes of soybean or peanut oil, cereal gluten, particularly wheat, rice or corn gluten, and lactic proteins, more particularly casein or lactoserum proteins for example. Isolates or concentrates of vegetable or animal proteins, for example, may also be used.

It is preferred to prepare an aqueous suspension of such a material which has a dry matter content of 10 to 40%.

The pH of this suspension is adjusted to a value of 6.0 to 11.0 and preferably to a value of 8.0 to 10.0, for example by addition of sodium hydroxide.

A protease is added to the suspension, the protease having an activity of, for example, 0.2 to 12 AU per 100 g dry matter of the suspension. This protease is preferably selected from the group consisting of neutral or alkaline proteases of bacterial origin (produced for example by *B. Licheniformis* or *B. subtilis*) or fungal origin (produced for example by *A. oryzae* or *A. soyae*). Enzymes such as these are marketed, for example, under the name of NEUTRASE or ALCALASE by Novo Industri A/S, under the name of MKC-HT PROTEOLYTIC 200 or MKC/Protease/L330 by Miles Kali-Chemie GmbH & Co KG or under the name of COROLASE N, PN or 7089 by Röhm GmbH.

The suspension may be hydrolyzed for 2 to 8 h and preferably for 3 to 6 h at 50° to 75° C. and preferably at 61° to 68° C.

The pH then is adjusted to 4.6–6.5 and preferably to 4.9–5.9, for example by addition of hydrochloric, lactic, citric, phosphoric or acetic acid. The heat treatment step at this pH plays an important part in regard to the viscosity of the suspension and the solubility of the flavouring agent obtained in a preferred embodiment of the process in which the suspension is pressed after ripening, and the juice obtained is pasteurized and clarified. If the pH is adjusted to a value above 6.5, the flavouring agent shows excessive turbidity when diluted with water. If the pH is adjusted to a value below 4.6, the heat-treated suspension has a viscosity which makes it difficult to pump.

The heat treatment may be carried out, for example, in a double-jacketed tank, in a heat exchanger or by injection of steam. Depending on the method of heating selected, the temperature of the heat treatment may be between about 90° and 140° C. and the heat treatment time may be between about 10 s and 30 minutes, the shortest times corresponding to the highest temperatures and vice versa.

The heat-treated suspension then is cooled, for example to a temperature of 20° to 40° C. If the heat treatment is carried out by injection of steam, this cooling may be carried out by flashing which gives the flavouring agent finally obtained a more neutral taste.

Koji may then be added to the cooled suspension in a quantity of 2 to 50% by weight koji, based on dry matter of the suspension, the koji itself having a dry matter content of approximately 60 to 75% for example. The koji may have been prepared, for example, by mixing an oilseed or a cooked pulse, particularly soya or cooked haricot beans, with a cooked or roasted cereal, particularly crushed and roasted rice or wheat, in a quantity of 50 to 90 parts by weight dry matter of optionally defatted oilseed or pulse and 10 to 50 parts by weight cereal, leaving the mixture to cool to 20°-40° C., inoculating it with a koji culture and with a pure culture of $A.\ oryzae$ or $A.\ soyae$ spores in a quantity of 1 part by weight spore culture or powder to 1,000 to 10,000 parts by weight mixture and leaving the mixture to ferment for 30 to 50 h at 20° to 40° C. on traditional wattles, on a plate or in a commercial apparatus specially designed for this purpose with intermittment stirring and aeration.

After sodium chloride has been added to the suspension in such a quantity so that the suspension has a sodium chloride content of approximately 10 to 17% by weight for example, the suspension may be left to ripen under the effect of the enzymes in the koji, namely the enzymes which have been produced by the koji culture during fermentation of a mixture of cooked pulse or oilseed and cooked or roasted cereal for example.

In one embodiment of the process according to the invention, the suspension is left to ripen for 2 to 20 days, after which a flavouring agent having an agreeable and relatively neutral taste is obtained.

Another embodiment of the process according to the invention is characterized in that, after koji and sodium chloride have been added, the suspension is inoculated with a culture of halophilic yeast and left to ripen for 1 to 8 weeks at 20° to 40° C. A flavouring agent having a stronger taste is obtained in this way. In this particular embodiment of the process according to the invention, the suspension has a pH if from 4.9 to 5.9 and is preferably inoculated with 1 to 5% by volume of a culture of $Saccharomyces\ rouxii$ and/or $Torulopsis\ etchelsii$ containing approximately $10^7$ to $10^8$ cells of one or the other microorganism or of a mixture of these microorganisms per ml.

After the ripening step, a clear juice may be extracted from the suspension and may be used as a flavouring agent either as such or after various additional treatments. This juice may also be concentrated, dehydrated and reduced to powder.

To extract the clear juice, the suspension may be pressed after ripening, the insolubles removed and the juice obtained pasteurized and clarified. More particularly, the suspension may be pressed in a press capable of applying an adequate pressure of the order of 10 to 100 bar, such as for example a screw press or hydraulic press. The juice obtained may be pasteurized for 5 s to 30 mins. at a temperature of 75° to 140° C. and may then be clarified by passage through a filter paper or a synthetic membrane for example.

The clarified juice may then be concentrated to a dry matter content of approximately 60 to 85% by weight, for example by evaporation for about 1 to 8 h at a temperature of approximately 40° to 65° C. under a pressure of approximately 10 to 100 mbar.

The concentrated juice may also be dehydrated to a dry matter content of approximately 95 to 99% by weight, for example by drying for about 5 to 10 h at a temperature of approximately 60° to 80° C. under a pressure of 10 to 100 mbar. Finally, the dehydrated juice may be ground, for example in a hammer mill, to reduce it to powder.

The flavouring agent obtained by the process according to the invention in the form of a ripened aqueous suspension, a clear liquid, a concentrate or a powder may either be used as such for flavouring various dishes or as a basic ingredient in the composition of food products or may be used for the preparation of liquid, semi-liquid or dehydrated sauces and soups for example.

EXAMPLES

The process according to the invention is illustrated by the following Examples in which percentages and parts are by weight, unless otherwise stated.

EXAMPLE 1

An aqueous suspension of a defatted soya flour having a dry matter content of 23% is prepared. The pH of the suspension is adjusted to 10.0 by addition of NaOH. 0.6%, based on the dry matter content of the suspension, of a bacterial alkaline protease (produced by $B.\ licheniformis$) having an activity of 2.4 AU per g enzyme is added to the suspension. The suspension is then hydrolyzed with continuous stirring for 3 h at 68° C. in a jacketed tank.

The pH value of the hydrolyzed suspension is adjusted to 5.4 by addition of citric acid. The suspension is subjected to a heat treatment by injection of steam at 140° C. for 10 s. The suspension thus treated is cooled to 30°-35° C. by expansion to atmospheric pressure.

In addition, to prepare a koji, 1 part soybean oil cake is mixed with 1 part water, the mixture is cooked in an autoclave for 15 mins. at 120° C. and then cooled to 30° to 35° C. The cooked soya is mixed with crushed roasted wheat in a quantity of 70% soya dry matter to 30% dry matter of the roasted wheat. This mixture is inoculated with a koji culture in a quantity of 1 part spore culture or powder to 5,000 parts mixture. The mixture is left to ferment on wattles for a period of 44 h during which it is stirred twice in all and continuously aerated.

This koji is added to the suspension cooled to 30°-35° C. in a quantity of 20% koji, based on the dry matter content of the suspension. Sodium chloride is added in such a quantity that the suspension has a sodium chloride content of 14%. The suspension is left to ripen for 15 days at that temperature.

The suspension is pressed in a hydraulio press. The insoluble fractions are removed by sedimentation. The juice obtained is pasteurized for 30 mins. at 90° C. and then clarified by passage through a filter paper.

The liquid flavouring agent obtained has a dry matter content of approximately 28%, shows good clarity and fluidity and has an agreeable, relatively neutral taste free from any bitterness.

EXAMPLE 2

The procedure is as described in Example 1 up to formation of the cooled suspension containing koji and sodium chloride.

The pH of the suspension is adjusted to 5.4 by addition of citric acid.

The suspension is inoculated with 2% by volume of a mixed culture of *Saccharomyces rouxii* and *Torulopsis etchelsii* containing approximately $5.10^7$ cells of each of these microorganisms per ml. The suspension is then left to ripen for 4 weeks at 33° C.

After ripening, the suspension is pressed in a hydraulic press. The juice is collected, left standing for 3 days and the insoluble fractions which have sedimented are removed. The juice is pasteurized for 15 mins. at 95° C. and then clarified by passage through a filter paper.

The liquid flavouring agent obtained has a dry matter content of approximately 28 to 30%, perfect clarity, good fluidity and a stronger taste free from any bitterness.

EXAMPLE 3

The procedure is as described in Example 2, except that an aqueous suspension of a mixture of 60% defatted soya flour and 40% casein or lactoserum proteins is prepared.

The liquid flavouring agent obtained is comparable in its qualities with the flavouring agent obtained in Example 2.

EXAMPLE 4

The clarified juice obtained in Example 2 is concentrated at a temperature of approximately 60° C. under a pressure of 20 mbar to a dry matter content of approximately 75%.

The concentrated juice is then dehydrated to a dry matter content of 98% under reduced pressure in a dryer in which it is exposed to a temperature of approximately 70° C. under a pressure of 20 mbar.

The dehydrated juice is ground in a hammer mill provided with a 1 mm square-mesh sieve.

A flavouring agent is obtained in powder form and may be used as a seasoning or may be reconstituted by dispersion in water in a quantity of 1 part powder to 3 parts water for example. The flavouring agent thus reconstituted is comparable in its qualities with the product obtained in Example 1.

This liquid, concentrated or powder-form flavouring agent may be used equally well as such as an ingredient in the composition of food products. It may also be used as a starting material rich in free amino acids capable of reacting with reducing sugars to make bases for the preparation of sauces or soups.

We claim:

1. A process for the production of a flavoring agent comprising hydrolyzing an aqueous suspension of a protein material having a pH of from 6.0 to 11.0 with a protease selected from the group of proteases consisting of neutral and alkaline proteases having an activity of from 0.2 Anson units to 12 Anson units per 100 g dry matter of the suspension to solubilized protein in the suspension, heat-treating the hydrolyzed suspension at a pH of from 4.6 to 6.5 for from about 10 seconds to about 30 minutes at a temperature of from about 90° C. to about 140° C., cooling the heat-treated suspension and then treating the cooled suspension with enzymes obtained from koji to ripen the suspension to obtain a ripened suspension containing a flavoring agent.

2. A process according to claim 1 wherein koji is added to the cooled suspension to provide the enzymes to treat the cooled suspension.

3. A process according to claim 2 wherein the koji is added to the cooled suspension in an amount of from 2% to 50% koji by weight based on dry matter of the suspension.

4. A process according to claim 1 or 2 or 3 wherein the aqueous suspension is hydrolyzed for from 2 hours to 8 hours at a temperature of from 50° C. to 75° C.

5. A process according to claim 1 or 2 or 3 wherein the aqueous suspension of the protein material has a pH of from 8-10 and the hydrolyzed suspension is heat-treated at a pH of from 4.9 to 5.9.

6. A process according to claim 1 further comprising adding sodium chloride to the cooled suspension so that the suspension contains sodium chloride in an amount of from about 10% to 17% by weight.

7. A process according to claim 2 or 3 further comprising adding sodium chloride to the cooled suspension so that the suspension contains sodium chloride in an amount of from about 10% to 17% by weight.

8. A process according to claim 7 wherein the ripening treatment is carried out for form 2 days to 20 days at a temperature of from 20° C. to 40° C.

9. A process according to claim 7 further comprising adding a culture of halophilic yeast to the cooled suspension to treat the ripen the cooled suspension.

10. A process according to claim 9 wherein the cooled suspension has a pH of from 4.9 to 5.9.

11. A process according to claim 9 wherein the culture of the halophilic yeast is selected from the group of yeasts consisting of cultures of *Sacchromyces rouzii*, *Torulopsis etchelsii* and mixtures thereof containing from $10^7$ to $10^8$ cells per ml and is added to the cooled suspension in an amount of from 1% to 5% by volume.

12. A process according to claim 9 wherein the ripening is carried out for from 1 week to 8 weeks at a temperature of from 20° C. to 40° C.

13. A process according to claim 1 or 2 or 3 further comprising pressing the ripened suspension to obtain a juice and then pasteurizing the juice and clarifying the pasteurized juice.

14. A process according to claim 9 further comprising pressing the ripened suspension to obtain a juice and then pasteurizing the juice and clarifying the pasteurized juice.

* * * * *

UNITED STATES PATENT AND TRADEMARK OFFICE
CERTIFICATE OF CORRECTION

PATENT NO. : 5,141,757
DATED : August 25, 1992
INVENTOR(S) : Thang HO DAC, et al.

It is certified that error appears in the above-identified patent and that said Letters Patent is hereby corrected as shown below:

Column 2, line 52, change "Protease" to --PROTEASE--.

Column 3, line 53, change "if" to --of--.

Column 6, line 4 [line 7 of claim 1], change "solubilized" to --solubilize--.

Column 6, line 40 [line 3 of claim 9], change the first occurrence of "the" to --and--.

UNITED STATES PATENT AND TRADEMARK OFFICE
CERTIFICATE OF CORRECTION

PATENT NO.  : 5,141,757

DATED       : August 25, 1992     Page 2 of 2

INVENTOR(S) : Thang HO DAC, et al.

It is certified that error appears in the above-identified patent and that said Letters Patent is hereby corrected as shown below:

Column 6, line 45 [line 3 of claim 11], "Sacchromyces rouzii" should read --Saccharomyces rouxii--.

Signed and Sealed this

Thirty-first Day of August, 1993

*Attest:*

BRUCE LEHMAN

*Attesting Officer*         *Commissioner of Patents and Trademarks*